United States Patent
Jafary (10) Patent No.: US 9,877,733 B1
(45) Date of Patent: Jan. 30, 2018

(54) ANTI-NECROSIS TOURNIQUET DEVICE

(71) Applicant: Mohammad R. Jafary, Toronto (CA)

(72) Inventor: Mohammad R. Jafary, Toronto (CA)

( * ) Notice: Subject to any disclaimer, the term of this patent is extended or adjusted under 35 U.S.C. 154(b) by 390 days.

(21) Appl. No.: 14/792,993

(22) Filed: Jul. 7, 2015

Related U.S. Application Data (60) Provisional application No. 62/049,634, filed on Sep. 12, 2014.

(51) Int. Cl.
*A61B 17/00* (2006.01)
*A61B 17/135* (2006.01)
*A61B 17/132* (2006.01)
*A61B 19/00* (2006.01)

(52) U.S. Cl.
CPC ........ *A61B 17/1355* (2013.01); *A61B 17/135* (2013.01); *A61B 17/1322* (2013.01); *A61B 17/1325* (2013.01); *A61B 19/30* (2013.01); *A61B 2019/302* (2013.01)

(58) Field of Classification Search
CPC .............. A61B 17/132; A61B 17/1322; A61B 17/1325; A61B 17/135; A61B 17/1355; A61B 19/30; A61B 2019/302
See application file for complete search history.

(56) References Cited

U.S. PATENT DOCUMENTS

| | | | | |
|---|---|---|---|---|
| 4,106,002 A * | 8/1978 | Hogue, Jr. | ............. | A61B 5/022 340/573.1 |
| 4,294,261 A * | 10/1981 | Baker | ................... | A61B 5/022 600/499 |
| 4,321,929 A * | 3/1982 | Lemelson | .............. | A61B 5/022 600/301 |
| 4,520,819 A * | 6/1985 | Birmingham | ...... | A61B 17/1355 606/202 |
| 4,548,198 A * | 10/1985 | Manes | ............... | A61B 17/1355 606/202 |
| 4,671,290 A * | 6/1987 | Miller | ................ | A61B 5/02225 600/494 |
| 5,181,522 A * | 1/1993 | McEwen | ................. | A61B 5/03 600/561 |
| 6,051,016 A * | 4/2000 | Mesaros | ............ | A61B 17/1355 606/202 |
| 6,213,939 B1 * | 4/2001 | McEwen | ............ | A61B 17/1355 600/202 |
| 6,231,507 B1 * | 5/2001 | Zikorus | .................... | A61B 8/04 600/437 |
| 7,479,154 B2 | 1/2009 | McEwen et al. | | |

(Continued)

*Primary Examiner* — Eric Rosen
*Assistant Examiner* — Son Dang
(74) *Attorney, Agent, or Firm* — Robert C. Montgomery; Montgomery Patent and Design, L.P.

(57) ABSTRACT

An anti-necrosis tourniquet device utilizes an air compressor, programmable through a microprocessor, to enable a user to set periodic cycles of increased and decreased pressure in a pressure cuff as a temporary measure to address a severely hemorrhaging wound on an extremity. When a situation arises to employ a tourniquet, the cuff is applied to a proximal region of the wound. The device is activated to increase pressure in the cuff to occlude the flow of blood to the wound for a programmed period of time after which the program decreases pressure in the cuff to supply blood to the wounded extremity for another selected time period to obviate necrosis of the tissue. This modulated cycle is repeated until a patient receives full medical treatment.

22 Claims, 5 Drawing Sheets

(56) References Cited

U.S. PATENT DOCUMENTS

| | | | | |
|---|---|---|---|---|
| 8,048,105 B2* | 11/2011 | McEwen | A61B 17/1355 | 606/201 |
| 2003/0036771 A1* | 2/2003 | McEwen | A61B 17/135 | 606/202 |
| 2003/0167070 A1* | 9/2003 | McEwen | A61B 17/135 | 606/203 |
| 2003/0233061 A1* | 12/2003 | Hui | A61H 9/0078 | 601/152 |
| 2005/0143689 A1* | 6/2005 | Ramsey, III | A61M 25/10 | 604/103.13 |
| 2006/0224181 A1* | 10/2006 | McEwen | A61B 17/1355 | 606/202 |
| 2006/0253150 A1* | 11/2006 | McEwen | A61B 5/02233 | 606/202 |
| 2008/0119785 A1* | 5/2008 | Ramsey | A61B 17/12136 | 604/98.01 |
| 2008/0262533 A1* | 10/2008 | McEwen | A61B 17/1355 | 606/202 |
| 2009/0124912 A1* | 5/2009 | McEwen | A61B 17/135 | 600/495 |
| 2010/0191277 A1* | 7/2010 | McEwen | A61B 8/06 | 606/202 |
| 2010/0204726 A1* | 8/2010 | McEwen | A61B 17/1355 | 606/202 |
| 2010/0211096 A1* | 8/2010 | McEwen | A61B 17/1355 | 606/203 |
| 2011/0238107 A1* | 9/2011 | Raheman | A61B 5/412 | 606/202 |
| 2012/0215253 A1* | 8/2012 | McEwen | A61B 17/135 | 606/202 |
| 2013/0211445 A1* | 8/2013 | McEwen | A61B 17/1355 | 606/202 |
| 2016/0008005 A1* | 1/2016 | McEwen | A61B 5/02233 | 606/202 |
| 2017/0112504 A1* | 4/2017 | McEwen | A61B 17/1355 | |

* cited by examiner

ANTI-NECROSIS TOURNIQUET DEVICE

RELATED APPLICATIONS

The present invention was first described in and claims the benefit of U.S. Provisional Application No. 62/049,634 filed Sep. 12, 2014, the entire disclosures of which are incorporated herein by reference.

FIELD OF THE INVENTION

The present invention relates generally to a tourniquet device that utilizes an air compressor to set periodic cycles of increased and decreased pressure in a pressure cuff.

BACKGROUND OF THE INVENTION

The standard treatment for traumatic injuries to limb areas with large amounts of bleeding is to apply a tourniquet until proper medical treatment such as surgery can be performed. However the process of stopping the bleeding with a traditional tourniquet often requires stopping all blood flow to any bodily region subsequent to the limb. If left unchecked, such cessation of blood flow can cause necrosis of tissues, nerve damage, and even result in limb death resulting in amputation.

Therefore, when using a tourniquet, trained personnel are taught to periodically release the pressure to let a small amount of blood through to keep the downstream tissues supplied with oxygenated blood. Unfortunately, in many emergency situations, there is either no one or to few people present to continuously monitor the pressure of a tourniquet. Similar problems exist in large trauma centers, on ambulances, and military combat situations.

Accordingly, there exists a need for a means by which a tourniquet can be monitored in an automatic and foolproof manner. The use of the tourniquet device provides the ability to stop excessive bleeding in limb areas in emergency situations without worry of causing additional injuries due to necrosis.

SUMMARY OF THE INVENTION

The inventor has recognized the aforementioned inherent problems and lack in the art and observed that there is a need for an anti-necrosis tourniquet device.

It is therefore an object of the invention to provide a tourniquet comprising a cuff, an air compressor in pneumatic communication with the cuff, a pressure sensor in pneumatic communication with the air compressor and a control module in electrical communication with the air compressor and the pressure sensor. The control module provides a selectable means for setting, maintaining, and varying an air flow generated by the air compressor and delivered to the cuff based on a high pressure level, a high pressure time, a low pressure level and a low pressure time. The air compressor is secured within the control module and the cuff is configured to be wrapped around a body part of a patient.

The control module comprises a case which comprises a planar bottom, a front wall, a rear wall and a pair of vertical sidewalls formed perpendicularly along horizontal edges of the bottom to define a hollow interior, an interactive digital display located on one of the walls of the case, a keypad located adjacent to the display, a circuit board located within the interior, a power source located within the interior, a microprocessor located within the interior, a discharge valve located within the interior and in pneumatic communication with the air compressor, an accumulator located within the interior and in pneumatic communication with the discharge valve and a supply connector located on one of the walls of the case and in pneumatic communication with the accumulator and the discharge valve to the case. The control module also comprises a cover removably attached and at least one hinged angular support bracket projecting outwardly. The circuit board is in electrical communication with the power source, the interactive digital display, the keypad, the microprocessor and the discharge valve.

The air compressor is secured within the case. The air compressor is controlled by the microprocessor and the air compressor delivers the air flow to the cuff sufficient to occlude a flow of blood of the body part below the cuff. The pressure sensor comprises a pressure transducer. The power source is an internal rechargeable battery. The power source is an external power supply via a receptacle. To the case is secured a handle.

The tourniquet further comprises an air hose. The first end of the air hose comprises a first hose connector capable of being removably connected to the supply connector and a second end of the air hose comprises a second hose connector capable of being removably connected to a cuff connector of the cuff. The cuff is a rectangular air bladder. The cuff further comprises an adjustment mechanism for adjusting a length thereof. The hinged angular support bracket is a formed metal loop with corrosion resist plating.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY 10 anti-necrosis tourniquet system
16 tourniquet
20 restrictive cuff
22 hook-and-loop fastener
24 cuff connector
26 cover
28 cylinder
30 air hose
32 first end
34 first hose connector
36 second end
38 second hose connector
40 control module
42 case
46 bottom 48 cover
50 handle
52 sidewall
54 interior
56 footpad
58 angular support bracket
62 front face
64 display
66 supply connector
68 rear face
70 keypad
72 power button
74 set button
76 start/increment button
78 disconnect/decrement button
79 indicia
92 receptacle
94 battery
96 battery charger
100 air compressor
102 air line
104 pressure sensor
106 discharge valve
108 accumulator
112 circuit board
114 microprocessor
124 alternate microprocessor
130 alternate keypad
132 start button
134 suspend button
136 upper limb button
138 lower limb button
210 high pressure level
220 high pressure time period
230 low pressure level
240 low pressure time period

DETAILED DESCRIPTION OF THE PREFERRED EMBODIMENT

Figure 3:
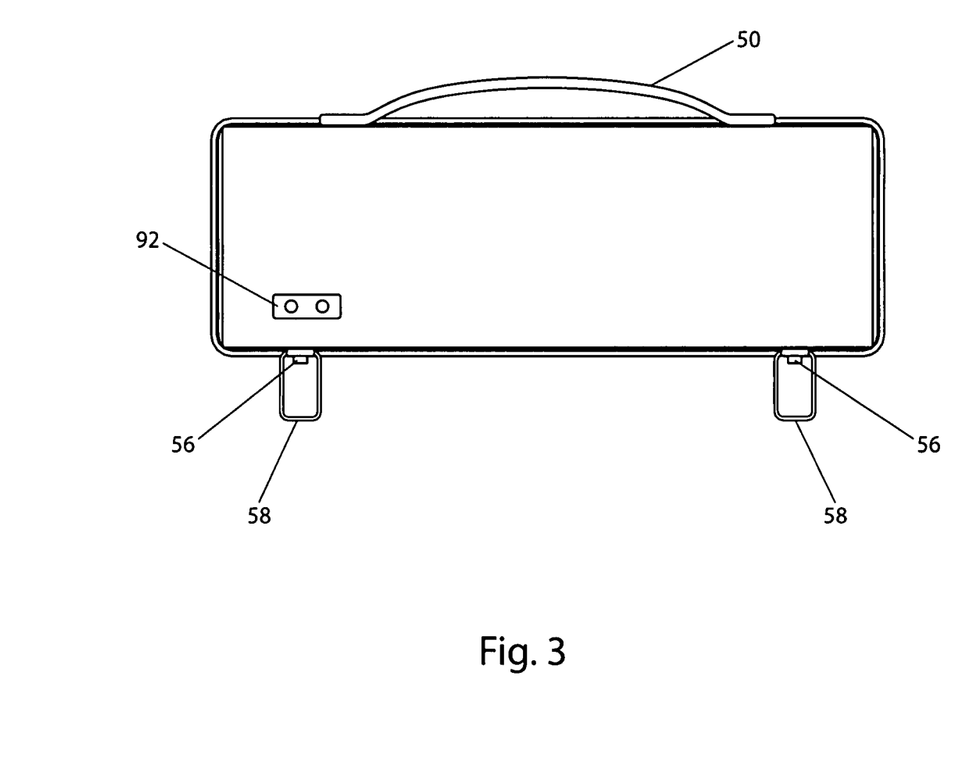
FIG. 3 is an isometric view of the rear exterior of the case 42.
Figure 4:
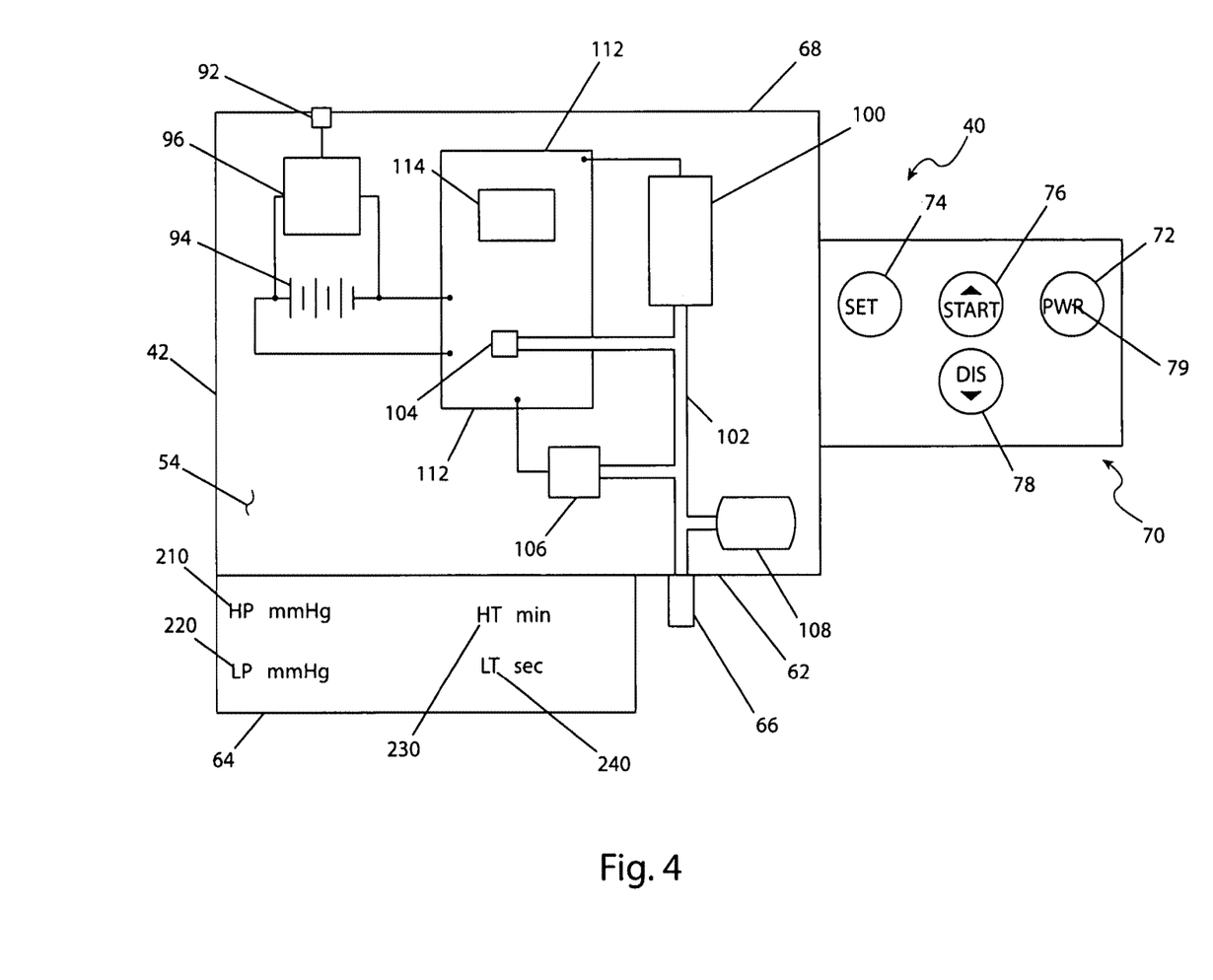
FIG. 4 is an operational block diagram of the system 10 in accordance with the preferred embodiment of the present invention; and, FIG. 5 is an operational block diagram of the system 10 in accordance with an alternate embodiment of the present invention.
Figure 5:
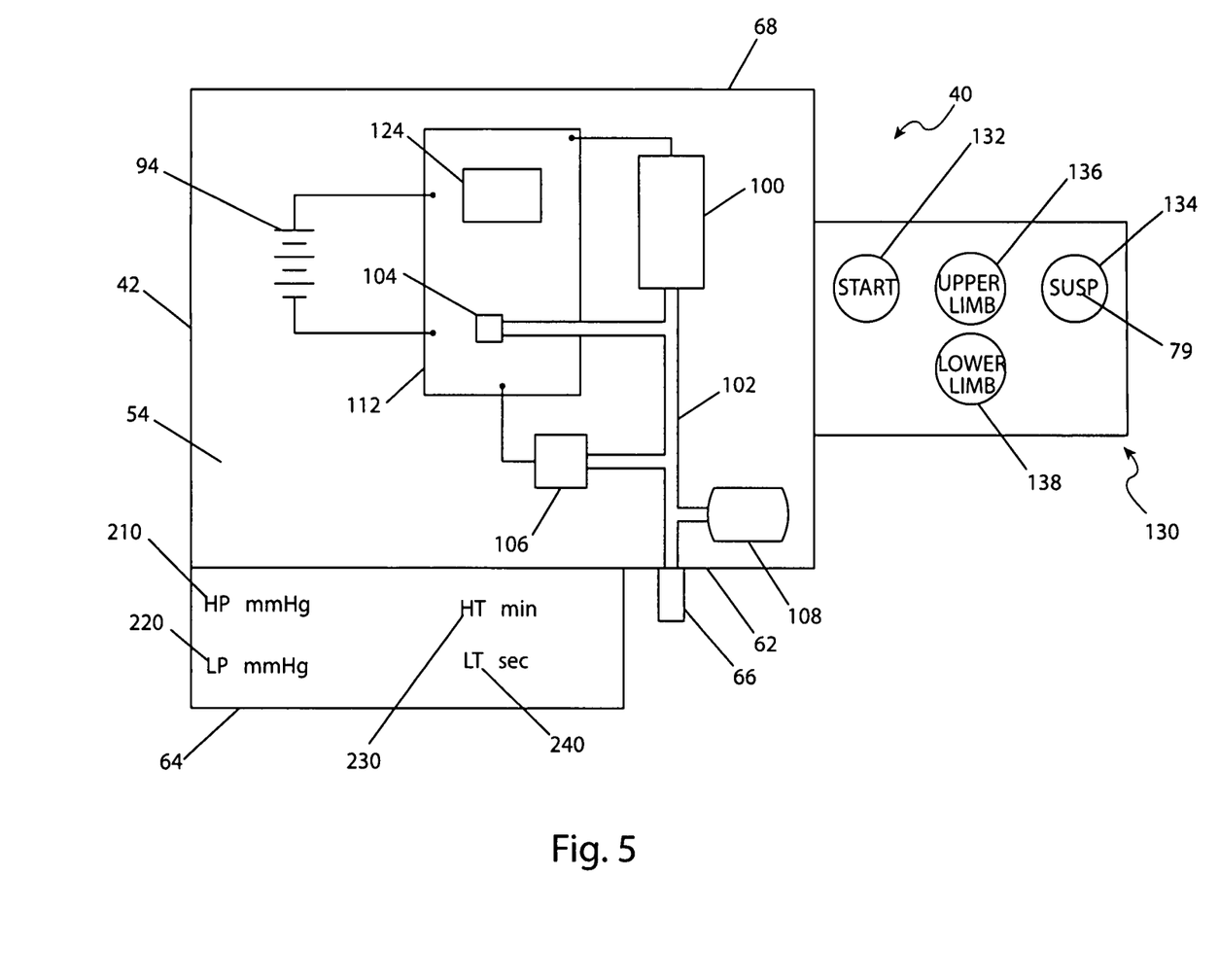

The best mode for carrying out the invention is presented in terms of its preferred embodiment, herein depicted within FIGS. 1 through 4, and an alternate embodiment, herein illustrated within FIG. 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes an anti-necrosis tourniquet (herein referred to as the "system") 10, which provides a means to apply potentially life-saving emergency medical treatment to the victim of a severely hemorrhaging extremity wound by placing a tourniquet 16 on the extremity which has the ability to alternately apply pressure, by means of a pneumatic restrictive cuff 20, to stop the flow of blood to the injury for a selected time period so as to reduce blood loss and then permit the flow of blood to the extremity for another selected period of time, by reducing the air pressure in the restrictive cuff 20, to obviate necrosis of the tissue in that extremity. The system 10 is provided with a programmable control module 40 which houses a microprocessor 112 containing the control logic for setting, maintaining, and varying the air pressure to the restrictive cuff 20, as well as an air compressor 100, and other ancillary equipment for achieving and monitoring that pressure. An alternate embodiment is envisioned to be provided with operating parameters which are pre-programmed into an alternate microprocessor 124 to more narrowly control the system 10 to a specific individual having a site-specific injury. It should be noted that since the size of the users to which this system 10 may be useful can vary considerably, there must be a range of sizes applicable to certain components of the system 10 implicit in any embodiment without limiting the scope of the invention.

Figure 1:
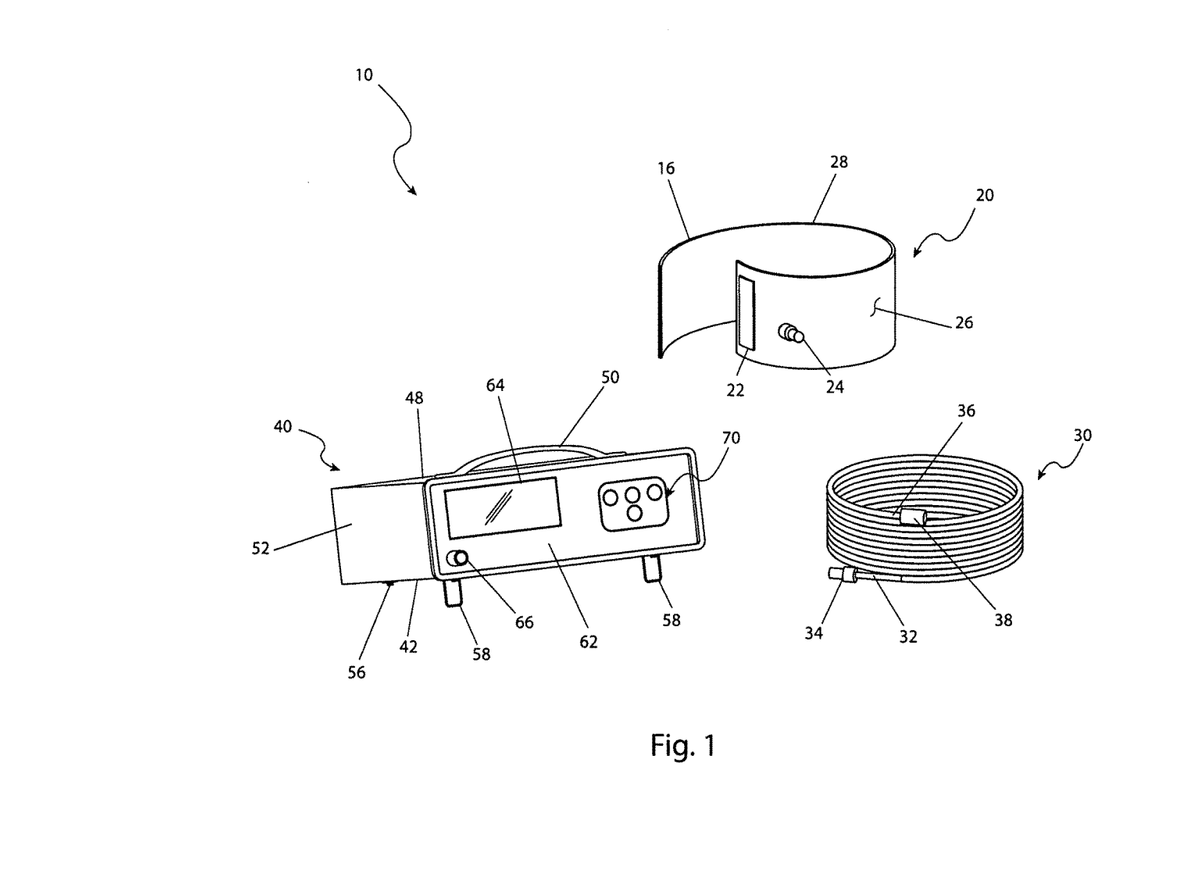
FIG. 1 is an isometric view of an anti-necrosis tourniquet device 10 in accordance with the preferred embodiment of the present invention.

Referring now to FIG. 1, an isometric view of the system 10 according to the preferred embodiment of the present invention, is disclosed. The system 10 includes a control module 40, a restrictive cuff 20, and an interconnecting air hose 30. The restrictive cuff 20 is generally a rectangular air bladder composed of a resilient polymer material which is intended to be wrapped circumferentially around a lower, or an upper, extremity of a trauma victim to form a cylinder 28. The restrictive cuff 20 is preferably provided with a hook-and loop fastener 22, such as VELCRO®, so as to be able to adjustably secure the restrictive cuff 20 to the extremity as described. Disposed along an outer cylindrical surface of the restrictive cuff 20 is a cuff connector 24 which is a pneumatic fitting to enable the removable connection of an air hose 30 for the purpose of injecting air into the bladder, or removing air from the bladder as necessary. The inflatable air bladder may be provided with any type of textile cover 26 to improve the comfort of a fit around the extremity or to provide some measure of abuse protection for the bladder.

The air hose 30 is preferably a silicone hose having an interior diameter and wall thickness commensurate with the operating pressures and flow rates of the system 10. The length of the air hose 30 in a preferred embodiment would be sufficient to accommodate a patient lying in a prone position and having the control module 40 located on a support structure several feet away with adequate length to allow an attending medical technician ample space to work around the patient. A first end 32 of the air hose 30 is provided with a first hose connector 34 capable of being removably connected to a supply connector 66 preferably located on a front face 62 of the control module 40, as depicted in FIG. 1. A second end 36 of the air hose 30 is provided with a similar or complimentary second hose connector 38 capable of being removably coupled to the cuff connector 24 on the restrictive cuff 20. Many types and sizes of such connectors 24, 34, 38, and 66 are commercially available from several suppliers and should not be considered as limiting the scope of the system 10.

Figure 2:
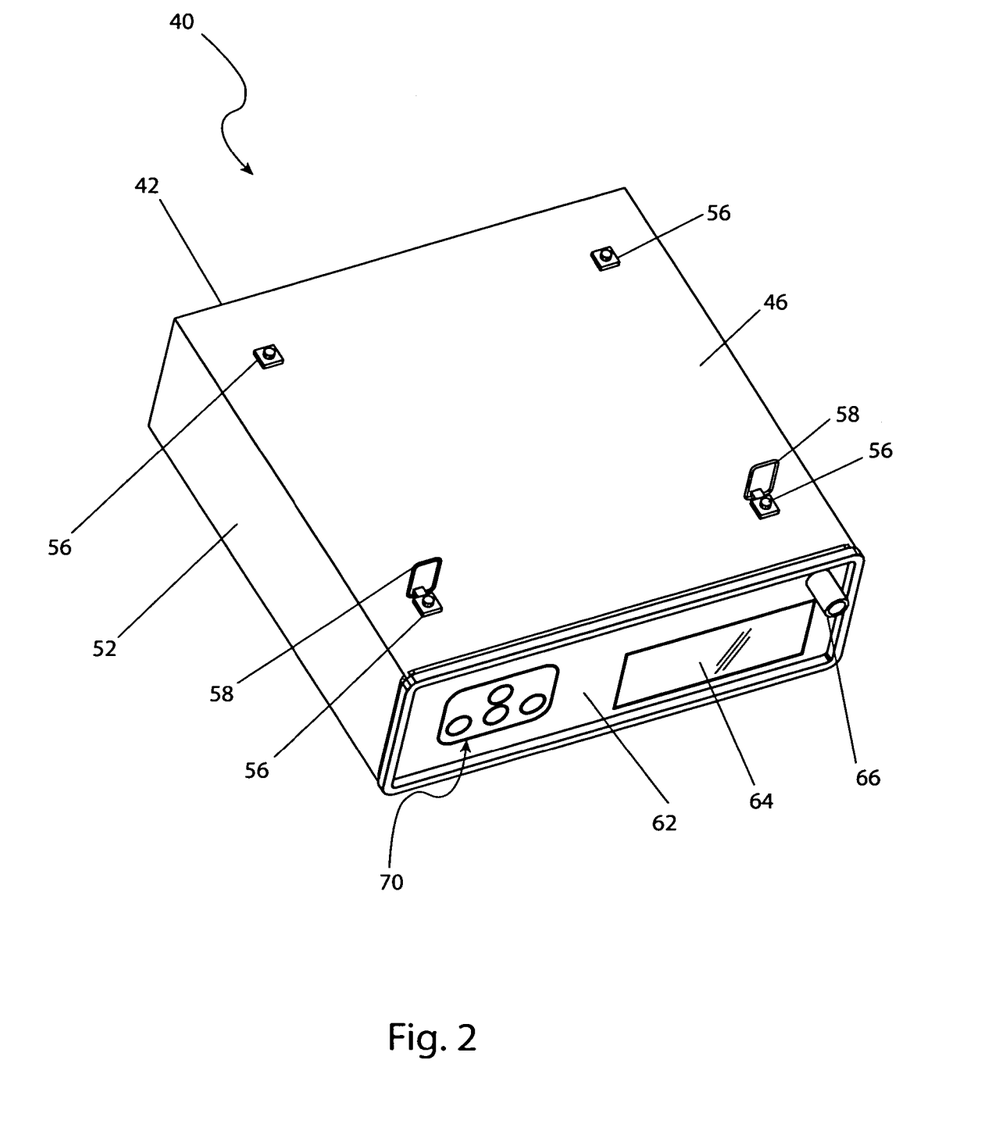
FIG. 2 is an isometric view of the bottom 46 of the case 42 of the system 10 in accordance with the preferred embodiment of the present invention.

Referring now to FIGS. 2 and 3, the control module 40 includes a case 42 having a front face 62 with a display 64 and a keypad 70, an internal rechargeable battery 94, an air compressor 100, and a microprocessor 112. The case 42 is preferably a metal enclosure with a protective coating, generally configured to be a rectangular polyhedron having a length, width, and height sufficient to accommodate the components to be placed therein. The case 42 is comprised of a planar bottom 46 with four (4) planar vertical sidewalls 52 formed perpendicularly along the horizontal edges of the bottom 46 in one (1) piece to define a hollow interior 54. The case 42 is provided with a removable cover 48 to isolate the interior 54 while allowing provisional access for assembly and servicing of internal components. The sidewalls 52 may be sealed along all vertical abutting edges with any of a variety of polymeric materials, or by mechanical means, to further isolate the interior 54 from ambient environmental conditions, such as elevated moisture levels or dust. It is understood that other materials, such as rigid thermoplastics or composite materials, and other methods of fabrication, may be utilized in the construction of the case 42 without limiting the scope of the system 10.

Disposed along a first vertical sidewall 52 is a front face 62 provided with an interactive digital display 64 and a keypad 70 for user control of the system 10. A rear face 68, located on an opposing parallel sidewall 52 from the front face 62 is provided with a receptacle 92 for the insertion and retention of a power cord jack. In a preferred embodiment, the power supply is comprised of a 12-volt/14-volt direct current electrical supply from an external source, such as an automobile electrical system. It is envisioned that a commercially available power cord with an included transformer and current rectifier may also be employed for powering the system 10 and recharging the internal battery 94. A supply connector 66, as previously discussed, is preferably located on the front face 62 of the control module 40 to removably attach a first hose connector 34 of the air hose 30 to the air supply and control circuit of the control module 40. Disposed on the exterior of the bottom 46, as depicted in FIG. 2, is a plurality of rubber or rubber-like footpads 56 intended to provide increased frictional force to obviate any relative motion between the control module 40 and a support surface. The bottom 46 of the case 42 may also be provided with one (1) or more hinged angular support brackets 58 to selectively elevate the front face 62 relative to the rear face 68 to improve the visibility of the display 64 to a user. The angular support bracket 58 is configured to be a formed metal loop, having a protective plating to inhibit corrosion, capable of maintaining a stowed position against the bottom 46 of the case 42 as well as a deployed position with the longitudinal axis of the angular support bracket 58 approximately perpendicular to the bottom 46 of the case 42. It is envisioned that in some embodiments at least one (1) carrying handle 50 may be attached to some portion of the case 42 to facilitate the conveyance of the control module 40 with a patient who is being transported on a gurney or a stretcher.

Referring now to FIG. 4, an operational block diagram of the system 10, according to the preferred embodiment of the present invention, is disclosed. Contained within the control module 40 and in electrical communication with an external power supply via the receptacle 92 is a battery charger 96 with over-current protection incorporated to recharge the battery 94. The battery 94 is preferably a NiMh storage cell; however, any rechargeable, dry-cell device capable of electrochemically delivering a sufficient level of electrical power to energize all of the components of the electrical circuit, using any current battery technology, may be utilized.

The circuit board 112 is in electrical communication with the battery 94 or the external power supply, as well as a microprocessor 114, an air compressor 100, a pressure sensor 104, a discharge valve 106, the display 64 and the keypad 70. The air compressor 100 is physically located within the case 42 of the control module 40 and provides an air supply, at a rated flow up to a maximum pressure level for the inflation of the restrictive cuff 20 via the air hose 30. The air compressor 100 is any commercially available combination of a small-voltage, direct current motor coupled to an air compressor having an internal construction capable of delivering the requisite air flow to inflate the restrictive cuff 20 within an acceptable period of time and elevating that volume of air to a pressure level necessary to occlude the flow of blood in any human extremity by the constrictive force applied by the restrictive cuff 20. The preferred air compressor 100 for this system 10 is a model KPM32E-12A air compressor as manufactured by Koge Electronics, LTD.®. The air compressor 100 is controlled by the microprocessor 114 to activate when a flow of air is required to maintain the pressure set point of the high pressure level 210 or the low pressure level 230. The air compressor 100 is in pneumatic communication with the supply connector 66 on the front face 62, and hence the air hose 30 and the restrictive cuff 20, by means of an air line 102 within the control module 40. The air line 102 is preferably high strength polymeric tubing having an interior diameter and wall thickness commensurate with the operating pressures and flow rates of the system 10. The air line 102 is attached to the various pneumatic components such as the air compressor 100, the pressure sensor 104, and the discharge valve 106. The air pressure within the system 10 at any point in time is monitored by the pressure sensor 104 located on the circuit board 112. The pressure sensor 104 is a standard, commercially available pressure transducer which is in pneumatic communication with the pneumatic components of the system and translates any pressure to an electrical signal in communication with the microprocessor 114. In use, the air compressor 100 is activated to supply air to the restrictive cuff 20, via the supply connector 55 and the air hose 30, resulting in the inflation thereof up to a high pressure level 210 set point programmed into the microprocessor 114 in a procedure to be detailed later. When the high pressure level 210 set point is achieved, as measured by the pressure sensor 104, the air compressor 100 will be deactivated. The pressure sensor 104 will continue to measure the pneumatic pressure in the system 10 and provide continuous feedback, via an electrical potential, to the microprocessor 114. If at any point in the duration of the high pressure time period 220, as programmed into the microprocessor 114 by a user in a procedure to be detailed later, the pressure in the system falls below the high pressure level 210 set point, the air compressor 100 will again be reactivated to increase the pressure. An accumulator 108 is preferably incorporated into the pneumatic system prior to the supply connector 66 in order to reduce fluctuations in the air pressure caused by leakage in the system 10. The accumulator 108 is a vessel capable of storing a reservoir of air, typically involving a diaphragm under spring loading.

Upon the termination of the high pressure time period 220, the microprocessor 114 will send an electrical current to the discharge valve 106 which will, upon activation, release a certain volume of air from the restrictive cuff 20, via the air hose 30, the supply connector 66, and the air line 102, so as to permit a decrease of the air pressure in the restrictive cuff 20 to a level equal to the low pressure level 230 according to the value programmed into the microprocessor 114 in a procedure to be detailed later, and measured by the pressure sensor 104. The microprocessor 112 will keep the air compressor 100 deactivated during this transition period, but will permit the reactivation during the low pressure time period 240 as necessary. The microprocessor 114 will maintain the low pressure level 230 set point, as measured by the pressure sensor 104, during the low pressure time period 240 as programmed into the microprocessor by a procedure to be detailed later. It must be understood that the pressure of the entire pneumatic system will be reduced to this low pressure level 230 set point including pressure in the accumulator 108. At the termination of the low pressure time period 240, the microprocessor 114 will execute another cyclic iteration of the program.

The continued disclosure of the display 64 and the keypad 70, as depicted in FIG. 1, will incorporate a preferred procedure to program the microprocessor 114 as discussed previously. The display 64 on the front face 62 of the case 42 of the control module 40 is preferably a two-line LCD module capable of providing information pertinent to the programming and visualization of high pressure level 210, low pressure level 230, high pressure time period 220, and low pressure time period 240. It is understood that other interactive readout devices, such as a touch screen monitor with corresponding modifications to the keypad 70, may be utilized without limiting the scope of the system 10. The keypad 70 is configured to be a plurality of momentary contact switches, activated by touch, for the operation of the system 10 and the input of program parameters into the microprocessor 114. The preferred arrangement of the keypad 70 involves the utilization of four (4) switches as illustrated in FIG. 1. Indicia 79 on these buttons 72-78 may include symbols, abbreviations, or other alphanumeric character substitutions indicative of the function thereof. It is understood that any variation in the indicia 79 depicted does not modify the scope or intent of the system 10 and this embodiment does not preclude any other embodiments. A power button 72, preferably labeled as "PWR" is depressed to permit electrical energy from a standard power source to flow into the control module 40 in order to charge the on-board battery 94 and energize the circuit board 112. If the control module 40 is not connected to an external power source through the power cord 82, then the control module is powered only by the self-contained battery 94 with the depression of the power button 72. The activation of the power button 72 is confirmed by the appearance of some numerical value appearing in the display 64 for the values of high pressure level 210 as indicated by some equivalent abbreviation nomenclature such as "HP", high pressure time period 220 as "HT", low pressure level 230 by "LP", and low pressure time period 240 as "LT". This information may be presented in a two-line format. The high pressure level 210 ("HP") is the pneumatic pressure in the restrictive cuff 20, as measured in millimeters of a mercury column (mmHg) of a manometer at the pressure sensor 104, to occlude the flow of blood in the patient's extremity. The high pressure time period 220 ("HT") is the time interval, as measured in minutes, for which the high pressure level 210 ("HP") will be exerted in the restrictive cuff 20. The low pressure level 230 ("LP") is the pneumatic pressure in the restrictive cuff 20, as measured in millimeters of a mercury column (mmHg) of a manometer at the pressure sensor 104, to allow the flow of blood to freely circulate within the patient's extremity. The low pressure time period 240 ("LT") is the time interval, as measured in seconds, for which the low pressure level 230 ("LP") will be exerted in the restrictive cuff 20 to permit blood to circulate within the patient's extremity. The microprocessor 114 will preferably be initially pre-programmed with certain values for these set points. In order to treat the patient immediately, the start/increment button 76 is depressed to activate the cyclic functioning of the system 10 utilizing whatever set points had previously been programmed into the microprocessor 114.

The programming of the microprocessor 114 can be altered as necessary by depressing the set button 74. Upon the initial depression of the set button 74, the display 64 will show a value for the high pressure level 210 ("HP") in a cyclic pattern of a numerical value followed by a blank value indicating that the value may be reset. This resetting of the set point value can be accomplished by increasing the set point value with a depression, or a series of depressions, of the start/increment button 76, or decreasing the set point value, as appropriate, by depressing the dual-function disconnect/decrement button 78. When the desired value of the set point of the high pressure level 210 ("HP") is cyclically shown in the display 64, that value can be entered by a second depression of the set button 74. This second depression of the set button 74 will write the selected value for the high pressure level 210 ("HP") into a permanent memory section of the microprocessor 114 thus replacing any value that had previously existed. This second depression of the set button 74 will simultaneously advance the program to the next set point to be entered, which will be the high pressure time period 220 ("HT"). Upon the second depression of the set button 74 the set point value of the high pressure level 210 ("HP") will be shown on the display 64 and the set point value of the high pressure time period 220 ("HT") will be cycling between some numerical value and a blank. The high pressure time period 220 ("HT) set point value can be reset by again depressing the start/increment button 76 to increase the time period, or depressing the disconnect/decrement button 78 to decrease the time period as deemed appropriate. The available range for the value of the high pressure time period 220 ("HT") is five to thirty minutes (5-30 min.). A value less than five minutes (5 min.) will not be accepted as a usable set point by the microprocessor 114. If the set point value of the high pressure time period 220 ("HT") exceeds thirty minutes (30 min.) the display 64 will preferably register "CON" indicating that the microprocessor 114 will exert a pressure level in the restrictive cuff 20 equivalent to the high pressure level 210 ("HP") set point and discontinue any cyclic reduction thereof. This mode of operation would continue in this manner until such time as the preferred programming of the microprocessor 114 could be aborted. A third depression of the set button 74 will write the selected value for the high pressure time period 220 ("HT") into a permanent memory section of the microprocessor 114 as well as advancing the program to the next set point to be entered, which will be the low pressure level 230 ("LP"). Upon the third depression of the set button 74 the set point values of the high pressure level 210 ("HP") and the high pressure time period 220 ("HT") will be shown on the display 64 and the set point value of the low pressure level 230 ("LP") will be cycling between some numerical value and a blank. This set point can be selected by the depression of the start/increment button 76 or the disconnect/decrement button 78 as previously described for the preceding set points. A fourth depression of the set button 74 will write the selected value for the low pressure level 230 ("LP") into a permanent memory section of the microprocessor 114 as well as advancing the program to the final set point to be entered, which will be the low pressure time period 240 ("LT"). The value for the low pressure time period 240 ("LT") will be blinking and can be reset by the depression of the start/increment button 76 or the disconnect/decrement button 78 as previously described for the preceding set points. A fifth depression of the set button 74 will write the selected value for the low pressure time period 240 ("LT") into a permanent memory section of the microprocessor 114 as well as conclude the programming of the microprocessor 114. This fifth depression of the set button 74 will preclude the use of the start/increment button 76 for incrementing any set point value and can only now be utilized to start the proper function of the system 10. The system 10 will not function in the intended manner to follow the pattern of alternately increasing the pneumatic pressure in the restrictive cuff 20 to occlude the flow of blood and decreasing the pressure in the restrictive cuff 20 to allow free circulation of blood within the extremity until the start/increment button 76 is depressed. After this final depression of the start/increment button 76 the system 10 will continue to function according to the logic of the microprocessor 114 utilizing the set point values programmed during the set-up procedure until such time as the disconnect/decrement button 78 is depressed. Upon this depression of the disconnect/decrement button 78 the control logic of the microprocessor 114 will be suspended and all of the pneumatic pressure in the restrictive cuff 20, as well as within the control module 40 will be exhausted to the atmosphere via the discharge valve 106. At this point the electrical power is still available to the circuit board 112 and the control logic of the microprocessor 114 can reinstitute the normal function of the system 10 according to the set point parameters previously programmed by the depression of the start/increment button 76. The depression of the power button 72 following the depression of the disconnect/decrement button 78 will suspend the transmission of electrical power to the system 10 and the restrictive cuff 20 may be disconnected from the air hose 30 and removed from the patient. It is understood that any variation in the preferred method of programming of set point variables or the sequence thereof does not modify the scope or intent of the system 10 and this embodiment does not preclude any other embodiments.

Referring now to FIG. 5, an operational block diagram of the system 10 in accordance with an alternate embodiment of the present invention, is disclosed. In an alternate embodiment the control module 40 is provided with an alternate microprocessor 124 and an alternate keypad 130. The basic function of the system 10 remains essentially the same with the restrictive cuff 20 being supplied with air, from the air compressor 100 through the air line 102, the supply connector 66, and the air hose 30, in an alternating pattern of high occlusion pressure for some period of time followed by a low pressure to allow blood circulation for a short period of time and repeating in that manner until a wound can be addressed by medical professionals in a proper setting. The major difference with the alternate embodiment, aside from deriving electrical power for the control module 40 only from a self-contained battery 94, is that the set points for the high pressure level 210 ("HL"), the high pressure time period 220 ("HT"), the low pressure level 230 ("LP"), and the low pressure time period 240 ("LT") would be incorporated into the control logic of the alternate microprocessor 124 so as to eliminate the need for a trained operator. The system 10 would be administered by the patient in the absence of other individuals. The alternate keypad 130 is configured to have a power button 72 to provide a means to turn the system 10 on and off. Additionally, the alternate keypad 130 will be equipped with an upper limb button 136, a lower limb button 138, a start button 132, and a suspend button 134. Indicia 79 on these buttons 132-138 may include symbols, abbreviations, or other alphanumeric character substitutions indicative of the function thereof. The upper limb button 136 will select the set points for the parameters 210-240 of the control logic based upon conditions as seen for a wound in an arm of a typical adult male patient. Other embodiments can be tailored to other typical patients. The lower limb button 138 will select the set points for the parameters 210-240 of the control logic based upon conditions as seen for a wound in a leg of a typical adult male patient. The start button 132 will allow the system 10 to begin a normal sequence of operation according to the set points of the variables 210-240 which were preprogrammed into the control logic of the alternate microprocessor 124 according to the selection of the upper limb button 136 or the lower limb button 138. In use, either the upper limb button 136 or the lower limb button 138, depending on the location of a wound, would be depressed prior to the engagement of the start button 132. Depression of the suspend button 134 will result in the control logic of the microprocessor 114 being stopped and all of the pneumatic pressure in the restrictive cuff 20, as well as within the control module 40 will be exhausted to the atmosphere via the discharge valve 106. At this point the electrical power is still available to the circuit board 112 and the control logic of the alternate microprocessor 124 can reinstitute the normal function of the system 10 according to the set point parameters previously selected by the depression of the upper limb button 136 or the lower limb button 138. The depression of the power button 72 following the depression of the suspend button 134 will turn off the system 10 and the restrictive cuff 20 may be disconnected from the air hose 30 and removed from the patient.

The preferred embodiment of the present invention can be utilized by a specially trained individual in a straightforward manner. After procurement of the system 10, it would be connected to an external power supply to allow the internal battery 94 to be charged to full capacity by the battery charger 96. The method of installing and utilizing the system 10 may be achieved by performing the following steps: placing the restrictive cuff 20 in a proximal position to a wound either on an upper or a lower extremity of a patient; engaging the hook-and-loop fastener 22 to secure the restrictive cuff 20 to the extremity; connecting the first hose connector 34 of the hose 30 to the supply connector 66 of the control module 40; connecting the second hose connector 38 of the hose to the cuff connector 24 of the restrictive cuff 20; depressing the power button 72 of the keypad 70 to turn on the system 10; manipulating the set button 74, the start/increment button 76, and the disconnect/decrement button 78 to program the high pressure level 210, the high pressure time period 220, the low pressure level 230, and the low pressure time period 240 parameters into the microprocessor 114 to define the system 10 operation according to the previously detailed procedure; depressing the start/increment button 76 to activate the programmed operation of the system; monitor the patient and attend to other medical needs as necessary until the patient is delivered to the location where proper medical treatment is available such as a hospital, clinic or the like; depress the disconnect/decrement button 76 after an alternate means of controlling bleeding from the wound or injury has been put in place; depress the power button 72 to turn off the device 10 and remove the restrictive cuff 20.

The alternate embodiment of the present invention can be utilized by an individual with limited medical training. It is anticipated that the alternate embodiment of the system 10 would be utilized in situations when the arrival of a trained medical professional could not be reasonably predicted and a wound, or injury, would exacerbate an already life-threatening situation, such as battlefield conditions. The method of installing and utilizing the alternate embodiment of the system 10 may be achieved by performing the following steps: placing the restrictive cuff 20 in a proximal position to a wound either on an upper or a lower extremity of a patient; engaging the hook-and-loop fastener 22 to secure the restrictive cuff 20 to the extremity; connecting the first hose connector 34 of the hose 30 to the supply connector 66 of the control module 40; connecting the second hose connector 38 of the hose to the cuff connector 24 of the restrictive cuff 20; depressing the power button 72 of the alternate keypad 130 to turn on the system 10; depressing the upper limb button 136 if the wound is located in an arm, or alternately depressing the lower limb button 138 if the wound is located in a leg; depressing the start button 132 to activate the programmed operation of the system and attempt to proceed to a location where trained medical assistance can be gained. A doctor or other trained medical personnel will turn the system 10 off and remove the restrictive cuff 20 after an alternate means of controlling bleeding for the wound is put in place. It is anticipated that in the utilization of the alternate embodiment of the system 10 the user and the patient may be the same individual.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A tourniquet, comprising:
a cuff;
an air compressor in pneumatic communication with said cuff;
a pressure sensor in pneumatic communication with said air compressor;
a control module in electrical communication with said air compressor and said pressure sensor; and,
wherein said control module is configured for setting, maintaining, and varying an air flow generated by said air compressor and delivered to said cuff based on a high pressure level, a high pressure time, a low pressure level and a low pressure time; wherein the high pressure level, high pressure time, low pressure level and low pressure time can be selected by a user;
wherein said air compressor is secured within said control module; and,
wherein said cuff is configured to be wrapped around a body part of a patient; wherein during the high pressure time, the control module is configured to activate the air flow when a flow of air is required to maintain pressure of the cuff at the high pressure level and the control module is configured to deactivate the air flow when the high pressure level is achieved; wherein upon termination of the high pressure time, the control module is configured to release air from the cuff to permit a decrease of air pressure in the cuff to a level equal to the low pressure level.

2. The tourniquet of claim 1, wherein said control module comprises:
a case comprising:
a planar bottom;
a front wall, a rear wall and a pair of vertical sidewalls formed perpendicularly along horizontal edges of said bottom to define a hollow interior;
an interactive digital display located on one of said walls of said case;
a keypad located adjacent to said display;
a circuit board located within said interior;
a power source located within said interior;
a microprocessor located within said interior;
a discharge valve located within said interior and in pneumatic communication with said air compressor;
an accumulator located within said interior and in pneumatic communication with said discharge valve; and,
a supply connector located on one of said walls of said case and in pneumatic communication with said accumulator and said discharge valve;
a cover removably attached to said case; and,
at least one outwardly projecting hinged angular support bracket;
wherein said circuit board is in electrical communication with said power source, said interactive digital display, said keypad, said microprocessor and said discharge valve.

3. The tourniquet of claim 2, wherein:
said air compressor is secured within said case;
said air compressor is controlled by said microprocessor; and,
said air compressor delivers said air flow to said cuff sufficient to occlude a flow of blood of said body part below said cuff.

4. The tourniquet of claim 2, wherein said pressure sensor comprises a pressure transducer.

5. The tourniquet of claim 2, wherein said power source is an internal rechargeable battery.

6. The tourniquet of claim 2, wherein said power source is an external power supply via a receptacle.

7. The tourniquet of claim 2, whereupon said case is secured a handle.

8. The tourniquet of claim 2, further comprising an air hose:
wherein a first end of said air hose comprises a first hose connector capable of being removably connected to said supply connector; and,
wherein a second end of said air hose comprises a second hose connector capable of being removably connected to a cuff connector of said cuff.

9. The tourniquet of claim 2, wherein said hinged angular support bracket is a formed metal loop with corrosion resist plating.

10. The tourniquet of claim 1, wherein said cuff is a rectangular air bladder.

11. The tourniquet of claim 1, wherein said cuff further comprises an adjustment mechanism for adjusting a length thereof.

12. A tourniquet, comprising:
a cuff;
an air compressor in pneumatic communication with said cuff;
a pressure sensor in pneumatic communication with said air compressor;
a control module in electrical communication with said air compressor and said pressure sensor; and,
wherein said control module is configured for setting, maintaining, and varying an air flow generated by said air compressor and delivered to said cuff based on a high pressure level, a high pressure time, a low pressure level and a low pressure time; wherein the high pressure level, high pressure time, low pressure level and low pressure time is preprogrammed;
wherein said air compressor is secured within said control module; and,
wherein said cuff is configured to be wrapped around a body part of a patient; wherein during the high pressure time, the control module is configured to activate the air flow when a flow of air is required to maintain pressure of the cuff at the high pressure level and the control module is configured to deactivate the air flow when the high pressure level is achieved; wherein upon termination of the high pressure time, the control module is configured to release air from the cuff to permit a decrease of air pressure in the cuff to a level equal to the low pressure level.

13. The tourniquet of claim 12, wherein said control module comprises:
   a case comprising:
      a planar bottom;
      a front wall, a rear wall and a pair of vertical sidewalls formed perpendicularly along horizontal edges of said bottom to define a hollow interior;
      an interactive digital display located on one of said walls of said case;
      a keypad located adjacent to said display;
      a circuit board located within said interior;
      a power source located within said interior;
      a microprocessor located within said interior;
      a discharge valve located within said interior and in pneumatic communication with said air compressor;
      an accumulator located within said interior and in pneumatic communication with said discharge valve; and,
      a supply connector located on one of said walls of said case and in pneumatic communication with said accumulator and said discharge valve;
   a cover removably attached to said case; and,
   at least one outwardly projecting hinged angular support bracket;
   wherein said circuit board is in electrical communication with said power source, said interactive digital display, said keypad, said microprocessor and said discharge valve.

14. The tourniquet of claim 13, wherein:
   said air compressor is secured within said case;
   said air compressor is controlled by said microprocessor; and,
   said air compressor delivers said air flow to said cuff sufficient to occlude a flow of said body part below said cuff.

15. The tourniquet of claim 13, wherein said pressure sensor comprises a pressure transducer.

16. The tourniquet of claim 13, wherein said power source is an internal rechargeable battery.

17. The tourniquet of claim 13, wherein said power source is an external power supply via a receptacle.

18. The tourniquet of claim 13, whereupon said case is secured a handle.

19. The tourniquet of claim 13, further comprising an air hose:
   wherein a first end of said air hose comprises a first hose connector capable of being removably connected to said supply connector; and,
   wherein a second end of said air hose comprises a second hose connector capable of being removably connected to a cuff connector of said cuff.

20. The tourniquet of claim 13, wherein said hinged angular support bracket is a formed metal loop with corrosion resist plating.

21. The tourniquet of claim 12, wherein said cuff is a rectangular air bladder.

22. The tourniquet of claim 12, wherein said cuff further comprises an adjustment mechanism for adjusting a length thereof.

* * * * *